(12) United States Patent
Dendukuri et al.

(10) Patent No.: US 10,465,164 B2
(45) Date of Patent: Nov. 5, 2019

(54) METHOD FOR EXTRACTING VIABLE SPERMS FROM A SEMEN SAMPLE

(71) Applicants: ACHIRA LABS PVT. LTD., Bangalore (IN); Vasan Satya Srini, Bangalore (IN)

(72) Inventors: Dhananjay Dendukuri, Bangalore (IN); Satish Kalme, Bangalore (IN); Vijetha Nagendra Prakash, Bangalore (IN); Gokul R Prasath, Bangalore (IN); Vasan Satya Srini, Bangalore (IN)

(73) Assignees: ACHIRA LABS PVT. LTD. (IN); VASAN SATYA SRINI (IN)

( * ) Notice: Subject to any disclaimer, the term of this patent is extended or adjusted under 35 U.S.C. 154(b) by 119 days.

(21) Appl. No.: 15/698,251

(22) Filed: Sep. 7, 2017

(65) Prior Publication Data

US 2018/0072987 A1    Mar. 15, 2018

(30) Foreign Application Priority Data

Sep. 9, 2016 (IN) .............................. 201641030947

(51) Int. Cl.
*C12N 5/076* (2010.01)
*C12N 5/071* (2010.01)

(52) U.S. Cl.
CPC ........... *C12N 5/0612* (2013.01); *C12N 5/061* (2013.01); *C12N 2531/00* (2013.01); *C12N 2533/80* (2013.01); *C12N 2537/00* (2013.01)

(58) Field of Classification Search
CPC ....... C12N 5/061; C12N 5/0612; A61K 35/52
See application file for complete search history.

(56) References Cited

U.S. PATENT DOCUMENTS

2004/0142384 A1* 7/2004 Cohen .............. G01N 33/54326
                                                                                    435/7.2
2006/0141512 A1   6/2006 Sinha et al.

FOREIGN PATENT DOCUMENTS

WO    WO 99/37147      *  7/1999  ............... A01N 1/02
WO    2015/132805 A2      9/2015

OTHER PUBLICATIONS

Diamandis et al., "The Biotin-(Strept)Avidin System: Principles and Applications in Biotechnology," *Clin. Chem.* 37(5):625-636, 1991.

* cited by examiner

*Primary Examiner* — Allison M Fox
(74) *Attorney, Agent, or Firm* — Seed IP Law Group LLP (57) ABSTRACT

The method provides a hyaluronic-acid binding based technique to separate functionally competent and mature sperm. The method for extracting viable sperms from a semen sample comprises incubating functionalized HA with functionalized paramagnetic beads to obtain a plurality of HA coated paramagnetic beads. The method further comprises incubating the plurality of HA coated paramagnetic beads with the semen sample to obtain a first population and a second population of sperm. The first population comprises sperm bound to the plurality of HA coated paramagnetic beads and the second population comprises sperms not bound to the plurality of HA coated paramagnetic beads. The method comprises magnetically separating the first population from the second population and separating sperms from the plurality of HA coated paramagnetic beads in the separated first population to obtain the viable sperms.

7 Claims, 8 Drawing Sheets

METHOD FOR EXTRACTING VIABLE SPERMS FROM A SEMEN SAMPLE

TECHNICAL FIELD

The invention relates generally to the field of assisted reproductive technology (ART) and more specifically to a method for extracting viable sperms from a semen sample.

BACKGROUND

Assisted reproductive technology (ART) has been a breakthrough in the treatment of infertility since the 1990s. ART options are generally provided to couples in a sequence starting from simple to more complicated techniques. Typically, the sequence is Intra-Uterine-Insemination (IUI), In-Vitro Fertilization (IVF), and Intra Cytoplasmic Sperm Injection (ICSI).

IUI is a simple procedure with less risks and ethical issues surrounding it. IUI is used in human infertility treatment by manually introducing sperms into the female reproductive tract. IUI, although less risky and complex, has shown low rates of success in ART. In comparison, IVF and ICSI have shown considerably more success than IUI. However, both IVF and ICSI are expensive techniques, thereby, reducing feasibility. Further, IVF and ICSI are associated with ethical issues.

In all three ART techniques as mentioned above, sperm count, motility, and morphology are routinely used in semen analysis to rule out male infertility and to isolate viable sperms. In the case of IUI, success rates of conception are directly related to the availability of semen sample of high sperm motility and concentration. Therefore, success rate of IUI is dependent of fertility of males. Hence, in most male infertility cases, IUI is not generally recommended. Further, for IVF and ICSI demand for isolation and processing of motile and viable sperms for infertility treatment is increasing. Sperm motility and viability depends on spermatogenesis. Studies have shown that when spermatogenesis is compromised, a great percentage of sperms in the ejaculate may show abnormalities that include membrane, mitochondrial, nuclear, and chromosomal anomalies.

In addition to isolating high motility and viability sperms from the semen sample, in ART techniques, sample preparation methods are also vital. Studies have shown that the seminal plasma may contain some components such as prostaglandins, which inhibit fertilization and pregnancy (Shivaji & Bhargava, 1987). Therefore, during sample preparation for ART seminal fluid has to be removed. Most methods of sample preparation for IUI prefer to dilute the semen with culture media and centrifuge it.

The basic technique of separating sperms of high motility is based on the conventional, "swim-up" (SU) technique, which depends on the active movement of sperms from a cell pellet into an overlaying medium; or the discontinuous density gradient (DG) centrifugation, which uses centrifugation of seminal plasma to separate cells by their density. DG centrifugation is used to separate motile spermatozoa from dead sperms, leukocytes, and the other components of the seminal plasma in cases of severe oligozoospermia, teratozoospermia or asthenozoospermia. Both these techniques separate sperms based on motility. This is because motility is important in natural conception, especially in case of IUI. After the sperm reaches the oocyte, functional properties of the sperm, such as acrosome status and DNA maturity, determine penetration of zona pellucida and fertilization of oocyte, leading to successful pregnancy.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

In one aspect, the invention provides a method for extracting motile sperms from a semen sample.

SU and DG techniques are commonly used techniques for separation of sperm and preparation of sample for ART based on motility and morphology of sperm. Of these, DG centrifugation is the preferred technique to separate a great number of motile spermatozoa from dead sperms, leukocytes, and other components of the seminal plasma in case of severe oligozoospermia, teratozoospermia, or asthenozoospermia. Both SU and DG techniques are important in isolation of motile and viable sperms for IUI so that the sperm reaches the oocyte. After the sperm reaches the oocyte, functional properties of the sperm, such as acrosome status and DNA maturity, determine fertilization of oocyte and consequentially a successful pregnancy.

Both SU and DG method use centrifugation to separate motile and viable sperms from semen sample. Centrifugation is known to cause cellular damage and DNA fragmentation. DNA fragmentation has been found to be detrimental to achieving and sustaining pregnancies and is associated with recurrent pregnancy loss. A four-fold increase in miscarriage risk has been reported in IVF and ICSI data regarding cases with elevated DNA fragmentation. As a result, morphology and DNA fragmentation index (DFI) are indirectly associated with the functionality of the sperm and have come to be established as markers for successful pregnancy outcomes. Sperms with fragmented DNA have been found to affect the time to pregnancy in IVF and implantation rates, and increases in miscarriage rates.

Successful conception depends on integrity of DNA of sperm and functional properties of the sperm. Therefore, tests beyond semen analysis have been developed to understand the deeper insight of male infertility. Viability, physiological stress tolerance, zona binding and sperm DNA fragmentation have been evaluated to assess the fertilization potential of the sperm.

Recent studies have shown that mature and viable sperms bind to hyaluronic acid or hyaluronan (HA) and that clinical pregnancy rates have improved with HA-selected sperm, when compared with the conventional sperm isolation techniques. Sperms that bind to HA denote their maturity, viability, and unreacted status of acrosome. Plasma membranes of spermatids, during spermatogenesis, have HA-binding sites. These HA binding sperms are associated with minimal abnormalities and increased cellular maturity. The presence of HA receptor on the plasma membrane of mature sperm has been utilized as a marker of sperm maturity and fertilizing ability. HA binding assay consisting of binding of mature sperm to HA coated glass or plastic surface is comparable to sperm-zona pellucida binding, and can be used for the selection of mature sperm for ART procedures. Sperms unable to bind to HA are more likely to have deficient membrane remodeling. Spermatozoa with dysmaturity with retained cytoplasm have been found to be deficient in zona pellucida binding. Dysmature sperms also exhibit increased rates of lipid peroxidation that leads to DNA fragmentation. The frequencies of sperm with chromosomal defects are reduced approximately fourfold to fivefold in HA-selected sperm compared with semen sperm. In view of these advantages, HA-selection of sperm is expected to become an efficient and routine sperm processing step in ART procedures.

Currently, two ready-to-use systems specially designed for sperm-HA binding selection are available: Preselective Intracytoplasmic Sperm Injection (PICSI) (MidAtlantic Diagnostic-ORIGIO) and SpermSlow (MediCult-ORIGIO). Despite advantages of these two sperm selection systems, there are some procedural disadvantages. For example, the PICSI dish requires skillful handling. HA microdots in PICSI dishes are crater-shaped and flexible. Hydrogel walls of the HA microdots can be pierced and torn. In addition, uneven hydration of the microdot may cause its edge to buckle and lift off the dish creating small "caves" which trap sperms. Selection of trapped sperms with unknown HA-binding status can lead to the same risks as that caused by immature sperm. In some cases, the entire microdot may detach from the surface and can be found to be covered with sperm which are not suitable for selection and isolation. SpermSlow is viscous media consisting mainly of HA, and is a natural alternative to polyvinylpyrrolidone (PVP). However, in this case also, there is a component of technician skill to manipulate the micro droplets. In addition, the relatively high cost factor and low yield of mature sperm make these techniques unsuitable for IVF and ICSI.

The method of the present subject matter provides a hyaluronic-acid (HA) binding based technique to separate functionally competent and mature sperm to enable faster processing in ART. The method for extracting viable sperms from a semen sample comprises incubating functionalized HA with functionalized paramagnetic beads to obtain a plurality of HA coated paramagnetic beads. Weight ratio range of functionalized HA to functionalized paramagnetic beads is 0.0041-0.05. The method further comprises incubating the plurality of HA coated paramagnetic beads with the semen sample to obtain a first population and a second population of sperm. Concentration of the plurality of HA coated paramagnetic beads to semen sample is in the range of 12-24 µg/mL. The first population comprises sperm bound to the plurality of HA coated paramagnetic beads and the second population comprises sperms not bound to the plurality of HA coated paramagnetic beads. The method comprises magnetically separating the first population from the second population and separating sperms from the plurality of HA coated paramagnetic beads in the separated first population to obtain the viable sperms.

The method described herein provides a safe and facile technique for extraction of hyaluronic acid or hyaluronan (HA) binding sperms without causing DNA fragmentation. The technique described herein limits centrifugation and prevents the iatrogenic failures of IVF associated with sperm preparation techniques.

Figure 1:
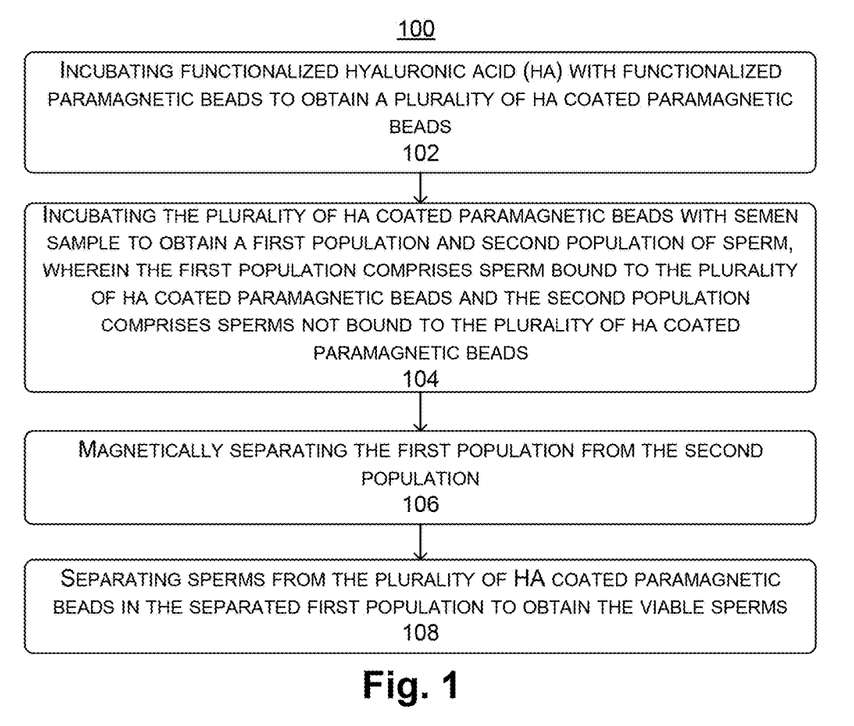
FIG. 1 is a flowchart of a method for extracting viable sperms from a semen sample, in accordance with an implementation of the present subject matter.
Figure 2A:
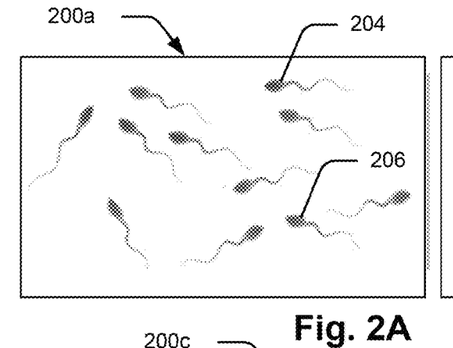
FIGS. 2A-2E are diagrammatic representations of respective reaction stages of the method for extracting viable sperms from the semen sample, in accordance with an implementation of the present subject matter.
Figure 2B:
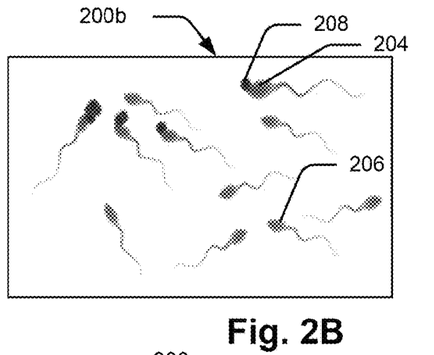
Figure 2C:
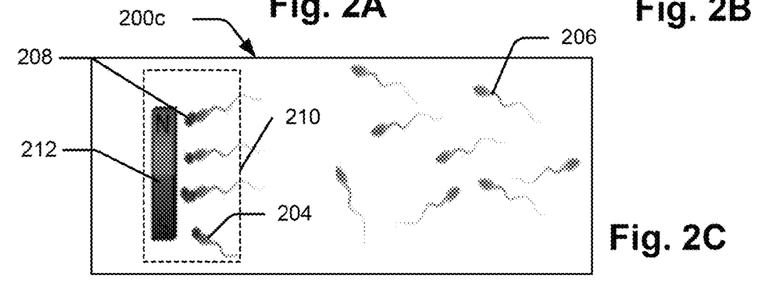
Figure 2D:
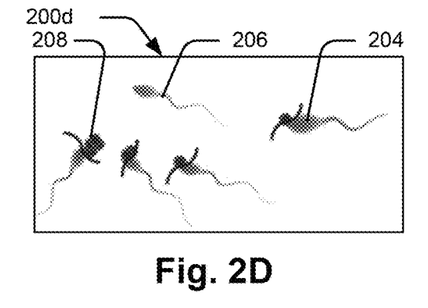
Figure 2E:
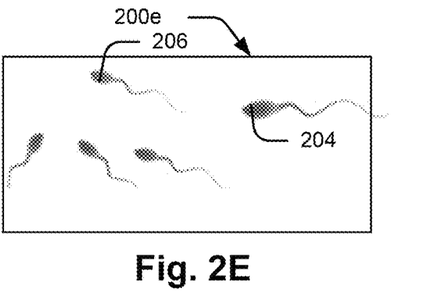

FIG. 1 depicts the method 100, in accordance with an implementation of the present subject matter. At block 102, the method 100 comprises incubating functionalized hyaluronic acid (HA) with functionalized paramagnetic beads to obtain a plurality of HA coated paramagnetic beads. HA, also called hyaluronan, is a mucopolysaccharide naturally occurring in extracellular matrix, synovial fluid, vitreous humor of the eye, and the like. It is made up of a poly-repeating disaccharide structure [(1→3)-/3-D-GlcNAc-(1→4)-/3-D-GlcA-], i.e. D-glucuronic acid and D-N-acetyl-glucosamine linked together through alternating 3-1,4 and 3-1,3 glycosidic bonds. It is known to have a large degree of polymerization up to the range of 104 disaccharides. Hyaluronan is predominantly anionic due to the carboxyl groups on the glucuronic acid that are negatively charged at physiological pH and ionic strength. HA has several biological functions including maintenance of elasto-viscosity of connective tissue, tissue hydration, water transport, receptor-mediated roles in cell detachment, mitosis, migration, tumor formation and metastasis, inflammation, lubrication of joints and muscles, etc. among several others. In an implementation, HA has a molecular mass of about 10 kDa with about 25 disaccharides in each molecule and 4.5-5% of HA is functionalized. In an implementation, HA is functionalized with biotin. In said implementation, functionalized HA comprises biotin bound to HA. Functionalizing HA with biotin modifies surface characteristic of HA to help in attachment of HA to Biotin Binding Proteins (BBPs). This further helps in anchoring functionalized HA to BBPs.

Paramagnetic materials have a small, positive susceptibility to magnetic fields. These materials are slightly attracted by a magnetic field and the material does not retain the magnetic properties when the external field is removed. In an implementation, the paramagnetic beads are selected from one of magnesium, molybdenum, lithium, tantalum, and combinations thereof. In an implementation, the paramagnetic beads are functionalized with BBPs selected from avidin, streptavidin, and combination thereof. In an implementation, the functionalized paramagnetic beads are stored in phosphate buffered saline (PBS) at a pH of about 7.2-7.4, where the PBS comprises 0.009-0.01% Tween 20, and 0.005-0.09% sodium azide as a preservative.

The functionalized HA is incubated with the functionalized paramagnetic beads to obtain the plurality of HA coated paramagnetic beads. In an implementation, the functionalized paramagnetic beads are pre-washed with PBS before incubating with the functionalized HA. Pre-washing with PBS helps in washing away sodium azide which can interfere with sperm extraction. In an implementation, the functionalized paramagnetic beads and functionalized HA are incubated for about 15 mins at about 37° C. In an implementation, weight ratio range of functionalized HA to functionalized paramagnetic beads is 0.0041-0.05. In an implementation, weight ratio range of functionalized HA to functionalized paramagnetic beads is 0.033. After incubation, obtained plurality of HA coated paramagnetic beads are washed again with the PBS buffer that includes Bovine Serum Albumin (BSA) prior to incubation with semen sample. BSA acts as a blocking agent and it reduces non-specific interaction of plurality of HA coated paramagnetic beads, for example, with plastic vial surfaces. In an implementation, functionalized HA comprises HA functionalized with biotin and functionalized paramagnetic beads comprise paramagnetic beads functionalized with streptavidin. In said implementation, the plurality of HA coated paramagnetic beads are formed due to affinity between biotin and streptavidin. It is to be understood that other BBPs can be used instead of streptavidin.

At step 104, the method 100 comprises incubating the plurality of HA coated paramagnetic beads with the semen sample to obtain a first population and a second population of sperm. In an implementation, concentration of the plurality of HA coated paramagnetic beads to semen sample is in the range of 12-24 µg/mL. In an implementation, concentration of the plurality of HA coated paramagnetic beads to semen sample is 18 µg/mL. The plurality of HA coated paramagnetic beads are, typically, stored in a buffer, for example, PBS. The semen sample is added to the plurality of HA coated paramagnetic beads contained in the buffer. In an implementation, incubating the plurality of HA coated paramagnetic beads with semen sample is performed for about 15 minutes at about 37° C.

The sperms with affinity for HA bind to the plurality of HA coated paramagnetic beads where viable sperms carry one or more of the plurality of HA coated paramagnetic beads attached to its head. The first population comprises sperm bound to the plurality of HA coated paramagnetic beads. The second population comprises sperms not bound to the plurality of HA coated paramagnetic beads. As previously explained, binding of sperm cells to HA indicates maturity, viability, and unreacted status of acrosome. Further, sperms cells that bind to HA are also associated with minimal abnormalities and have increased cellular maturity. Therefore, the first population of sperm cells are viable sperms that can be used for further processing for ART.

At step 106, the method 100 comprises magnetically separating the first population from the second population. In an implementation, the first population and second population are magnetically separated by placing on a magnetic stand. The first population is separated from the second population by virtue of attraction of paramagnetic beads to a magnet. The paramagnetic beads are attracted to the magnet while sperms of the second population remain free in the semen sample. The first population can be separated from the second population by pipetting, using flow properties, and combination of these techniques.

At step 108, the method 100 comprises separating sperms from the plurality of HA coated paramagnetic beads in the separated first population to obtain the viable sperms. Separating sperms from the plurality of HA coated paramagnetic beads in the separated first population comprises incubating the separated first population with Sperm Wash Media (SWM) and adding 90-110 U (Turbidity Reducing Unit (TRU)) of hyaluronidase enzyme during incubation of the plurality of HA coated paramagnetic beads with SWM to obtain released sperm. The SWM is a modified 4-(2-hydroxyethyl)-1-piperazineethanesulfonic acid (HEPES) buffer. HA is enzymatically degraded by hyaluronidase (HAase). Enzymatic degradation of HA of on the plurality of HA coated paramagnetic beads causes release of sperm that are were bound to HA. In an implementation, incubating the separated first population in SWM comprising HAase is performed for about 15 mins at about 37° C. at about pH of 7.0. Separating sperms from the plurality of HA coated paramagnetic beads in the separated first population further comprises magnetically separating the released sperms from the plurality of HA coated paramagnetic beads after incubation with to obtain the viable sperms. The obtained motile sperms are then assessed for their viability, motility, and total sperm count and can be used in ART.

FIGS. 2A-2E show the reaction stages of the method 100. Diagrammatic representation 200(*a*) depicts the semen sample with viable sperms 204 and non-viable sperms 206. Diagrammatic representation 200(*b*) represents viable sperms 204 binding to the plurality of HA coated paramagnetic beads 208. Diagrammatic representation 200(*c*) depicts the first population 210 being attracted to a magnet 212. Diagrammatic representation 200(*d*) depicts activity of HAase to release sperms from the plurality of HA coated paramagnetic beads 208 in the separated first population 210. Diagrammatic representation 200*e* depicts viable sperms 204 obtained by separating sperms from the plurality of HA coated paramagnetic beads 208 in the separated first population 210.

Figure 3:
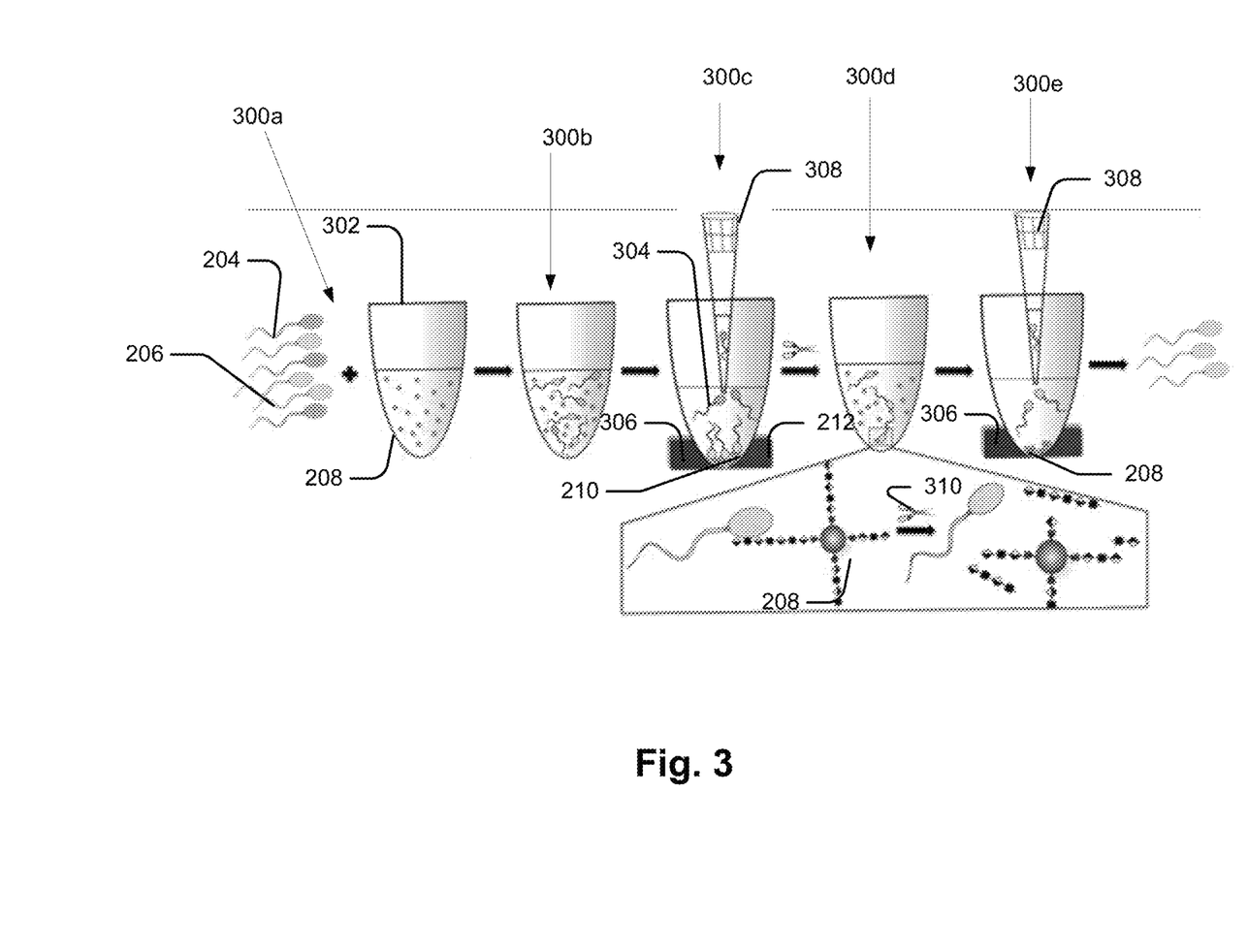
FIG. 3 provides pictorial representation of an implementation of the method, in accordance with an implementation of the present subject matter.

The method 100 described herein can be implemented using a microfluidic device or a magnetic stand that uses at least one of an electromagnetic or a fluidic stress applied on the first population 210. In one implementation, the method 100 can be conducted in an Eppendorf tube 302 as shown in FIG. 3. As shown in steps 300(a) of FIG. 3, semen sample, typically 100-1000 ml was added to the plurality of HA coated beads 208 contained in the Eppendorf tube 302 and incubated for about 15 minutes at about 37° C. The plurality of HA coated paramagnetic beads 208 can be suspended in a buffer, for example, Phosphate Buffer Saline (PBS). As shown in step 300(b), viable sperms 204, indicated using light green color, will bind to the plurality of HA coated paramagnetic beads 208 to form the first population 210 while the second population 304 comprising sperm not bound to the plurality of HA coated paramagnetic beads 208 remain free in the Eppendorf tube 302. As shown in step 300(c), the Eppendorf tube 302 can then be kept on a magnetic stand 306 to magnetically separate the first population 210 from the second population 304. It would be appreciated by those skilled in the art that once the Eppendorf tube 302 is placed on the magnetic stand 306, the paramagnetic beads in the solution are immediately drawn towards the surface of the magnet 212 and retained on a wall of the Eppendorf tube 302, thus, forming a supernatant that can be easily aspirated and separated from the plurality of HA coated paramagnetic beads 208 still in place on the wall of the Eppendorf tube 302. The second population 304 forms a supernatant and can be separated from the first population 210, for example, by using a micropipette 308.

As shown in step 300(d), sperms are separated from the plurality of HA coated paramagnetic beads 208 in the separated first population 210. The first population 210 is suspended in 100 μl of Sperm Wash Media (SWM) to which 100 units of hyaluronidase enzyme 310 is added (Hyaluronidase from bovine testes—Type IV-S, Sigma-Aldrich) and incubated for about 15 minutes at about 37° C. Hyaluronidase enzyme 310 releases sperms from the plurality of HA coated paramagnetic beads 208 to obtain viable sperms 204. As shown in step 300(e), the Eppendorf tube 302 can again be placed on the magnetic stand 306. Viable sperms 204 released from the plurality of HA coated paramagnetic beads 208 form the supernatant and can be collected, for example, by using the micropipette 308. The obtained viable sperms 204 can be further processed for viability characterization or for ART.

The present subject matter will now be illustrated with working examples, which are intended to illustrate the working of disclosure and not intended to be taken restrictively to imply any limitations on the scope of the present disclosure. Unless defined otherwise, all technical and scientific terms used herein have the same meaning as commonly understood to one of ordinary skill in the art to which this disclosure belongs. It is to be understood that this disclosure is not limited to the particular methods and experimental conditions described, as such methods and conditions may vary depending on the process and inputs used as will be easily understood by a person skilled in the art.

EXAMPLES

Reagents

Dynabeads MyOne Streptavidin C1, micron sized paramagnetic beads functionalized with streptavidin on the surface were purchased from Invitrogen®. It had a stock concentration of 10 mg/mL, with $7-10 \times 10^9$ beads per mL. The functionalized paramagnetic beads were contained in PBS buffer of pH of about 7.4 with 0.01% Tween-20 and 0.09% sodium azide as preservative. Biotinylated hyaluronic acid polymer of 10 kDa with 25 disaccharides in each molecule was purchased from Creative Pegworks®. About 5% of the HA chain was biotinylated. Hyaluronidase from bovine testes—Type IV-S (750-3000 units/mg) was purchased from Sigma-Aldrich®. DynaMag magnet was purchased from Invitrogen®. Improved Neubauer® chamber was purchased from Rohem®, India with 0.1 mm sample depth. Ferticult sperm wash media (SWM) was purchased from Fertipro®. Human semen samples that were diluted and cryopreserved after a density gradient wash were used for our analysis. The samples were obtained from donors at Manipal Ankur IVF center, Bangalore.

Example 1: Preparation of the Plurality of HA Coated Paramagnetic Beads

All the experiments were done in Eppendorf tubes 302, unless otherwise stated, which could be placed on the DynaMag magnet, hereinafter magnet 212, upon which the paramagnetic beads could be conveniently separated from the supernatant. It would be appreciated by those skilled in the art that once the Eppendorf tube 302 is placed on the magnet 306, the functionalized paramagnetic beads are immediately drawn towards the surface of the magnet 306 and retained on the Eppendorf tube 302, forming a supernatant that can be easily aspirated with the functionalized paramagnetic beads still retained in place. The functionalized paramagnetic beads can then be re-suspended in another solution in which they again disperse without showing any magnetic properties in absence of the magnetic field.

Before use, the functionalized paramagnetic beads, functionalized with streptavidin, hereinafter interchangeably referred to as streptavidin conjugated beads, were washed thrice with PBS buffer to remove any traces of sodium azide. Functionalized HA, functionalized with biotin, hereinafter referred to as biotinylated HA, was used to coat onto the streptavidin conjugated beads by incubating 2 μg biotinylated HA per 100 μg of streptavidin conjugated beads in 100 μT of PBS solution at room temperature for 30 min with gentle mixing. The obtained plurality of HA coated paramagnetic beads 208 were then washed 4-5 times with PBS containing 0.1% BSA and used in sperm binding experiments. The plurality of HA coated paramagnetic beads 208 were stored in PBS for stability.

Example 2: Magnet-Based (MG) Isolation of Method 100

All sperm samples were analyzed by following WHO guidelines (WHO, 2005). The cryopreserved samples were thawed and motility was checked by counting the sperms in a 20 μm deep wet preparation (using 10 μL, of sperm sample under a 22 mm×22 mm coverslip) at 400× magnification. Approximately 200 sperms were assessed per replicate for the percentage of sperms of different motile categories and calculated using following formula:

% motility=(motile sperm/total sperm)×100.

The sperm motility was graded as: progressive (PR) for actively moving sperms moving either linearly or in large circles; nonprogressive (NP) for sperms swimming in small circles or only the sperm tail beating is observed; and immotile (IM) sperms for sperms that show no movement.

Total motility is expressed as the sum of progressive and non-progressive motile sperms (i.e., Total motility=PR+NP). At least two replicates were counted for each sample and the values were recorded only when the difference between the replicates were in WHO recommended acceptance range. Contrarily, if the differences were not accepted, fresh replicates were made and new counts were taken from them. For those samples with very low sperm number, counts were taken from at least 10-15 fields and the average percentage was estimated from the total.

Sperm concentration of the sample was calculated by taking counts on the improved Neubauer counting chamber:

Sperm concentration=$(N/n) \times (1/20) \times$ dilution factor

Concentration is the total number [(N)=total sperms in 2 replicates], divided by the volume they were present in, i.e., [(n)=total number of rows present in the counted grids of 2 replicates] and the volume of the total number of rows counted (20 nL each for grids 4, 5, and 6). Counts were taken from at least two replicates for each sample and the values were recorded only when the differences between the replicates were accepted.

The method 100, hereinafter also interchangeably referred to as magnet-based (MG) isolation technique, was performed by mixing the plurality of HA coated paramagnetic beads 208 with the semen sample and incubating at 37° C. for 15 minutes. The sperms with affinity for HA were observed to bind to the plurality of HA coated paramagnetic beads 208, with the motile sperms seen to be carrying one or more of the plurality of HA coated paramagnetic beads 208 on their head. The sperms binding to the plurality of HA coated paramagnetic beads 208 were considered to be the first population 210, and the sperms that did not bind were considered to be the second population 304.

Figure 4:
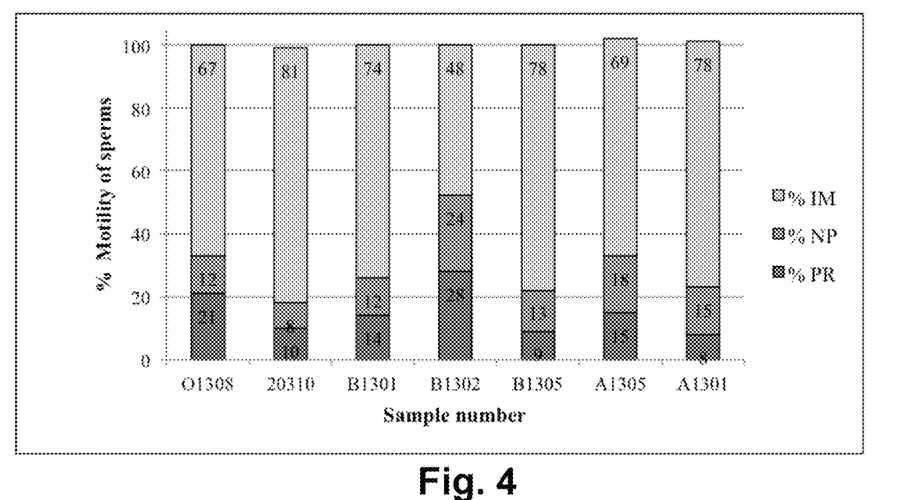
FIG. 4 represents the different types of sperms obtained from a first population, in accordance with an implementation of the present subject matter.

The first population 210 and second population 304 were separated by placing Eppendorf tube 302 on DynaMag magnet 212. The supernatant was pipetted out and the first population 210 was re-suspended in a sperm wash media (SWM). The enzyme hyaluronidase (100 U) was then added to the solution of the first population 210 and SWM and was incubated for about 15 minutes at about 37° C. to obtain sperms of interest. On separation, the supernatant contained the sperms of interest which were released from the plurality of HA coated paramagnetic beads 208 by the action of the enzyme on HA as explained previously. The plurality of HA coated paramagnetic beads 208 were washed twice with a small volume of SWM to release any sperms trapped. The collected sperm of interest were then assessed for their motility and total sperm count. FIG. 4 represents the different types of sperms in the collected sperms. Sperm count was taken after separating the first population 210 and the second population 304.

The effects of bead and HA concentration on sperm binding were studied. The effects of hyaluronidase concentration and incubation time on sperm release were also studied. The sperm populations were estimated by taking counts on improved Neubauer chamber as mentioned hereinabove.

Figure 5A:
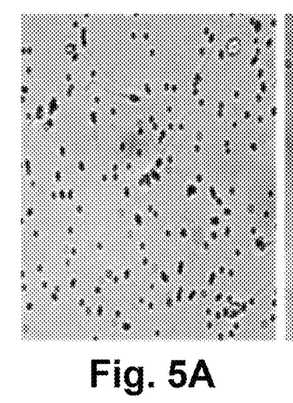
FIG. 5A is a microscopic view of sperms isolated using method of present subject matter, in accordance with an implementation of the present subject matter.
Figure 5B:
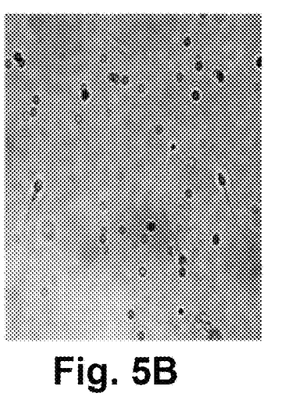
FIG. 5B is a microscopic view of native sperms, in accordance with an implementation of the present subject matter.
Figure 5C:
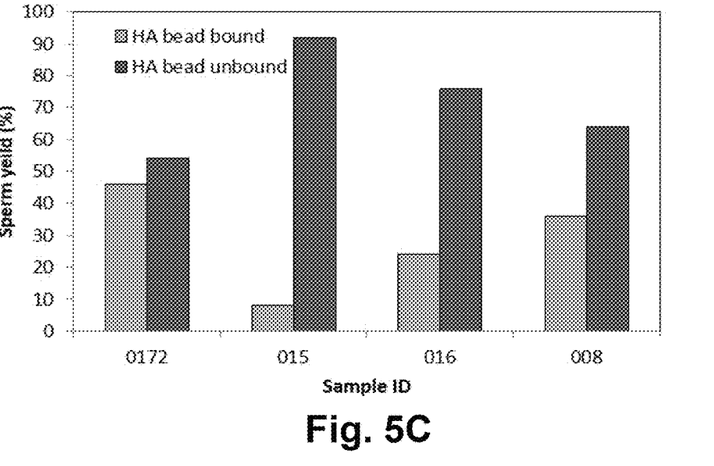
FIG. 5C is a graphical representation of sperm yield variation with variation in sample, in accordance with an implementation of the present subject matter.

Example 3: Effect of Concentration of the Plurality of HA Coated Paramagnetic Beads The first population 210 and second population 304 were observed under 400× magnification with the field as shown in FIG. 5A while FIG. 5B shows a control where the semen sample was not incubated with the plurality of HA coated paramagnetic beads 208. Sperms of the first population 210 were seen to be carrying one or more of the plurality of HA coated paramagnetic beads 208 on the surface of their head. The amount of sperms binding to plurality of HA coated paramagnetic beads 208 varied between samples, giving 8-46% (average 27.6%) bound sperms and 54-92% (average 72.4%) unbound sperms as illustrated in FIG. 5C. As can be understood from FIG. 4 and seen from FIG. 5A it was observed that both motile and immotile sperms were bound to the plurality of HA coated paramagnetic beads 208. Therefore, effect of concentration of various components on binding of motile sperms to the plurality of HA coated paramagnetic beads 208 was studied.

Figure 6A:
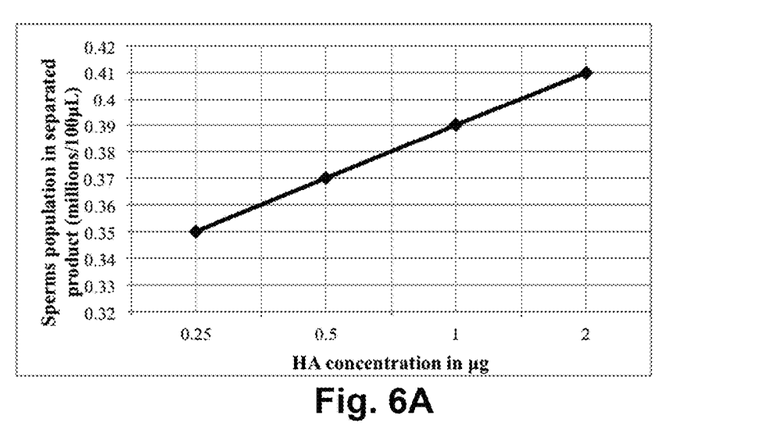
FIG. 6A represents variation in sperm binding capacity with concentration of hyaluronic acid, in accordance with an implementation of the present subject matter.

Biotinylated HA at 0.25-3 μg/60 μg streptavidin conjugated beads was immobilized in order to test its effect on increase in sperm binding. Sperm binding was found to be optimal at 2 μg of functionalized HA, which contained 200 μmol, i.e. $1.2 \times 10^{14}$ functionalized HA molecules. This amount of functionalized HA was found to be enough to saturate the binding sites of 60 μg of beads (~7-10×10$^6$ beads) since the binding capacity of 1 mg of beads was up to ~20 μg biotinylated HA. The sperm binding capacity of the plurality of HA coated paramagnetic beads 208 increased by 17% from 0.25 to 2 μg HA concentration as shown in FIG. 6A.

Figure 6B:
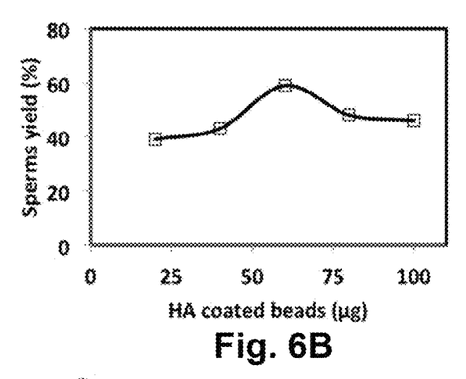
FIG. 6B is a graphical representation of bound sperm yield variation with variation of quantity of hyaluronic acid (HA)-coated beads, in accordance with an implementation of the present subject matter.
Figure 6C:
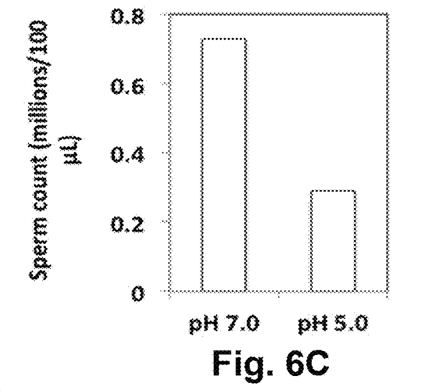
FIG. 6C is a graphical representation of bound sperm count variation with variation in pH of buffer, in accordance with an implementation of the present subject matter.

The percentage of bound sperms against 20-100 μg of the plurality of HA coated paramagnetic beads 208 showed a bell-shaped curve with increasing binding up to 60 μg beads in 100 μl of semen sample as illustrated in FIG. 6B. The optimum pH for release of HA bound sperm was 7.0, which released 152% more sperms as compare to HAase reaction at pH 5.0 as illustrated in FIG. 6C.

Figure 6D:
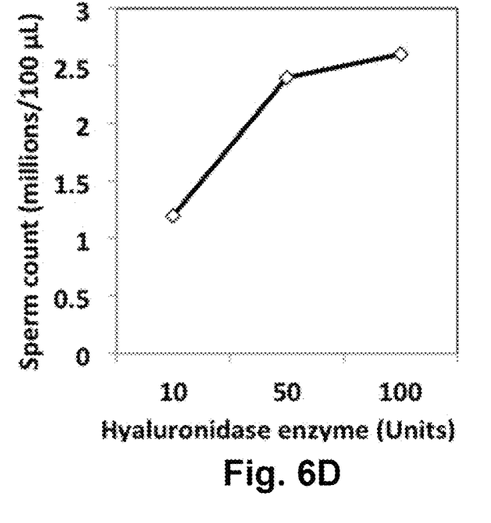
FIG. 6D is a graphical representation of bound sperm release count variation with variation in units of hyaluronidase, in accordance with an implantation of the present subject matter.

Further, three different concentrations of HAase, 10, 50, and 100 U, were tested for release of sperm from the first population 210 where the first population 210 was obtained by incubating 100 μl of sperm sample with the plurality of HA coated paramagnetic beads at 37° C. for 15 minutes. The sperm release was increased by 100% and 116% at 50 and 100 U of HA respectively as illustrated in FIG. 6D. 2.6 million sperms were obtained from 100 μl of semen sample using 100 U HAase enzyme.

Figure 6E:
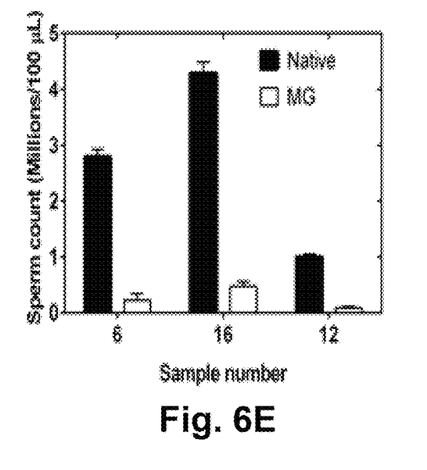
FIG. 6E is a graphical representation of sperm count variation with sample variation, in accordance with an implementation of the present subject matter.
Figure 6F:
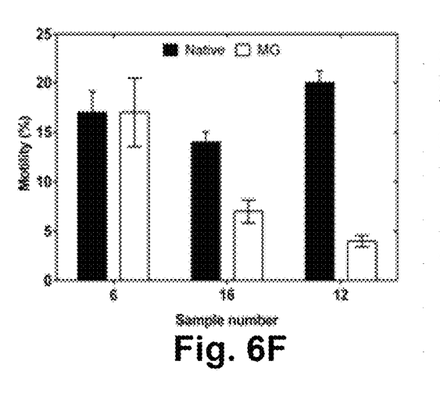
FIG. 6F is a graphical representation of motility variation with sample variation, in accordance with an implementation of the present subject matter.
Figure 6G:
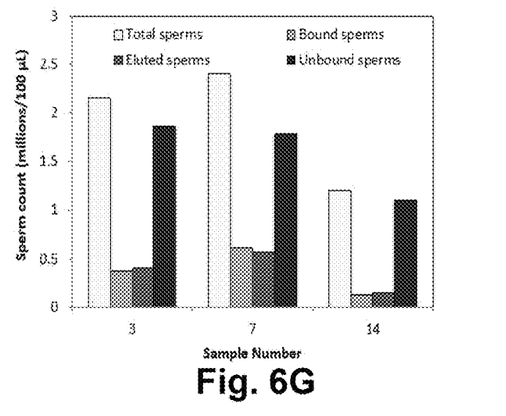
FIG. 6G is a graphical representation of sperm count (total, bound, eluted, and unbound) variation with sample, in accordance with an implementation of the present subject matter.

6-11% sperms were isolated using method 100 of present subject matter from samples containing 1.4-4.3 millions sperms/100 μl of sample as illustrated in FIG. 6E. The motility of the sperms obtained after the method 100 was sample dependent ranging from 20-100% motility of its initial sample (FIG. 6F). After enzymatic release of sperm from the plurality of HA coated paramagnetic beads 208, 12.5-24% (average 18.5%) sperms with ability to bind to HA were obtained as compared to total initial sperm population as illustrated in FIG. 6G.

Figure 6H:
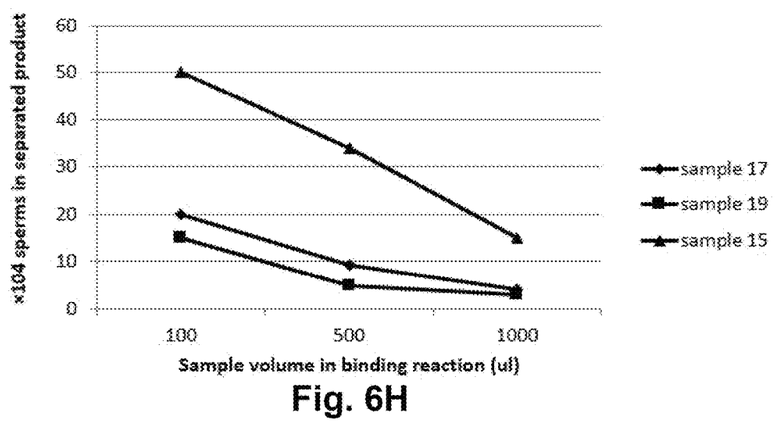
FIG. 6H depicts decrease in sperm binding with increase in semen sample volume, in accordance with an implementation of the present subject matter.

In 100 μl semen sample experiments, it was observed that sperms did not occupy all the HA coated paramagnetic beads 208. Therefore, effect of increasing semen sample was analyzed (100 μl, 500 μl, and 1 mL semen) at constant 60 μg of the plurality of HA coated paramagnetic beads 208. After the separation of the first population and second population 304, the plurality of HA coated paramagnetic beads 208 were re-suspended in 100 μl of SWM. 100 U of HAase enzyme was added and the dilution factor for the particular sample volume used was implicated to estimate the number of sperms that were recovered from the sample. Sperm recovery decreased by 70-80% with increase in semen volume as shown in FIG. 6H. The sperm recovery was decreased by 70-80% with increase in semen volume. Therefore, the beads volume was increased and binding was performed with 1 mL semen sample.

Figure 6I:
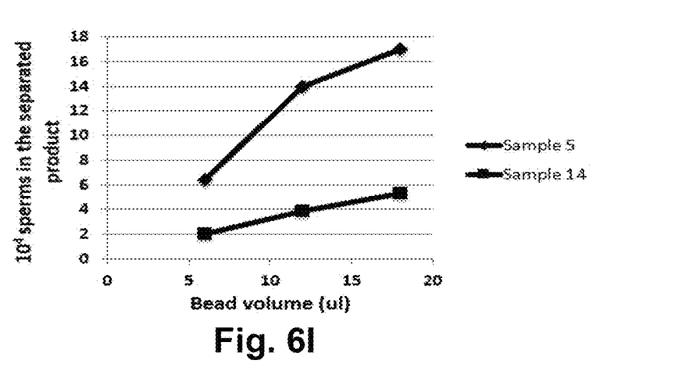
FIG. 6I depicts increase in sperm binding with increase in volume of plurality of HA coated paramagnetic beads, in accordance with an implementation of the present subject matter.

Three bead volumes (and weights) were used: 6 μL (60 μg beads), 12 μL (120 μg beads) and 18 μL (180 μg beads), with same amount of HA immobilized (2 μg HA on 60 μg beads). In this experiment, the beads were re-suspended in 100 μL of SWM and 100 U of HAase after the separation of bead-bound and unbound sperms. The sperm counts for the concentration were taken from this suspension and the dilution for 1 mL was worked out to obtain the approximate value for the number of sperms that were recovered from 1 mL using the particular amount of beads for binding. The increase in the recovery yield with the increase in bead volume used was as shown in FIG. 6I. 18 μL (corresponding to 180 μg) of beads was the highest volume used to elute the highest number of sperms when compared to the lower volumes. Further, weight of the plurality of HA coated paramagnetic beads 208 was optimized to 180 μg (corresponding to 18 μL) to process 1 ml semen sample, increasing sperm recovery by 2.65 times as shown in FIG. 6I.

Example 4: Steps in Comparison of Method 100 with SU and DG Methods

Example 4.1: Clinical Validation Study Design

The present study is a prospective, observational study of functional parameters of the sperm to evaluate the method 100 of the present subject matter. This multi-arm study compares swim up (SG), density gradient (DG), and method 100 (also referred to as MG based isolation) as well as unselected (native). The clinical validation study was designed to compare functional parameters of sperm, such as motility, morphology and DNA integrity of sperms separated by these techniques. The study was carried on for a period of 6 months.

The subject participation for this study was limited to husbands of infertile couples who were referred for semen analysis to the Andrology Laboratory. Additional inclusion criteria required that subjects must be in the age group of 18-45 years, enjoying normal health as per medical history and routine physical examinations, and be male partners of couple who could not conceive for at least one year. Men aged >45 years, diagnosed with diabetes or other serious, long term illnesses, those tested positive for HIV, HBV, HCV etc., and patients who may not be able to provide semen sample, based on their medical history and physical examination were excluded from the study. All the subjects included into the study signed an informed consent and provided a semen sample after 2-4 days abstinence.

Semen samples from fifty-five subjects (N=55) were processed. After liquefaction of the semen, a routine semen analysis was performed according to WHO 2010 guidelines, for the determination of sperm count, motility and morphology12. DNA Integrity of sperm in the native, unprocessed sample was determined using flow cytometry. Each semen sample was diluted to an initial concentration of 60 million/mL, and 0.5 mL portions were processed by each sperm separation technique, namely swim up (SU), density gradient (DG) and the method 100. Following separation, the above mentioned sperm characteristics were determined once again for comparison. This study design of comparison of the functional capacity of sperms from the same subject, separated by different techniques, limits patient-to-patient variations and facilitates good comparison of efficacy of these techniques.

HA binding capacity of sperms isolated by MG, DG and SU techniques was studied, briefly, sperms isolated by these techniques were incubated with HA coated beads as mentioned above and viability, HOS test and sperm count was reported.

Example 4.2: Swim-Up (SU) Technique Protocol

In a centrifuge tube, 1 mL of patient semen sample was taken in an Eppendorf tube 302 and 2 mL of SWM (FertiPro NV, Belgium) was added to it. The mixture was shaken well and centrifuged for 10 min at 1,200 rpm. The supernatant was discarded to remove debris, pus cells, etc. A layer of SWM was created over the pellet by slow addition along the sides of the Eppendorf tube. The Eppendorf tube 302 was placed in an incubator, inclined at an angle around 45° to increase the surface area between the medium and the semen, at 37° C. for 45 min. After incubation, the tubes were returned to the vertical position and 1 ml of the supernatant was gently removed, aspirating the sperms from the upper meniscus downwards with a sterile pipette. The supernatant was pipetted into a new tube for further characterization.

Example 4.3: Density Gradient (DG) Technique Protocol

A two-layer density-gradient formed by an upper layer of 40% (v/v) and a lower layer of 80% (v/v) SWM (FertiPro NV, Belgium) incubated at 37° C. was used. In a round bottom tube labeled with the patient details, 1 ml of 80% gradient media was taken and 1 mL of 40% gradient media was gently placed as a top layer. On top of the 40% layer, a layer of 1 mL of semen sample was placed without disturbing the interface. The tube was centrifuged for 15 minutes at 1200 rpm (300 xg). Motile spermatozoa migrate through the distance between the layers and are concentrated in the lower layer (80%). After centrifugation, most of the supernatant is gently removed and the pellet was re-suspended in 2 ml of HEPES based Sperm-Wash media (Sure Life, Singapore) and centrifuged at 1200 rpm for 7 min to remove traces of density gradient media. At the end of centrifugation, the supernatant was discarded and the final pellet was re-suspended in SWM and used for the determination of motility, morphology and DFI.

Example 4.4: Sperm Count Protocol

Concentration of sperm in unstained preparations of native semen sample (pre-process) and after separation by SU, DG and method 100 was determined as per WHO 2010 guidelines.

Rapid progressive motility, defined as >25 μm/s, at 37° C., was determined according to WHO 2010 guidelines for the native and post-process sperms, in order to compare the separation techniques.

Example 4.5: Morphology Study Protocol

Percentage of normal and abnormal forms of sperms in native as well as post-process samples was determined according to Kruger's strict criteria classification.

Example 4.6: Hypo-Osmotic Swelling Test

The Hypo-osmotic swelling (HOS) test was performed by mixing 0.1 mL aliquots of semen with 1.0 mL of a 150 mmol/kg hypo-osmotic solution (FertiPro NV, Belgium). The mixture was incubated for 30 min at 37° C. in 5% $CO_2$ and 95% air. After incubation, 0.2 mL of the mixture was placed on a slide, mounted with a cover slip and examined immediately at a magnification of ×400 under a phase contrast microscope. The percentage of reacted sperm (curled tails) and non-reacted sperm (non-curled tails) were assessed by counting a minimum of 100 sperms.

Example 4.7: DNA Integrity Study Protocol

DNA integrity of sperm in native as well as post-process samples, was evaluated in terms of DNA Fragmentation index (DFI) determined by flow cytometry (FCM) method. DFI for native, unprocessed sperms was corrected using the percentage of viable sperms 204 in the sample, previously determined by HOS test. Classification of DFI data was based on the following criteria of extent of DNA fragmentation: (i) Good: DFI≤15%, (ii) Moderate: DFI 15%-30%, and (iii) Poor: DFI>30%.

Example 4.8: Statistical Analysis

Sample size was calculated based on pilot experimental data. At a typical statistical significance level of 5% (alpha=0.05), an accepted power of the trial to be 0.8 (80%), and using a moderate success rates for the control and the experimental (method 100) groups, the sample size required per group was calculated to be 54. All statistical analyses were performed using IBM SPSS Statistics ver. 20.0 (IBM Corp, USA). Descriptive statistics for each outcome variable including mean, median, SD, range etc. was evaluated for each separation technique group as well as native sample. Comparison of means of all the outcome variables, i.e., motility (% progressive motility), morphology (% normal forms), and DNA integrity (DFI) was performed using Student's t-test and one-way ANOVA with post-hoc Tukey tests, at 95% CI (P<0.05 taken to be statistically significant).

Example 4.9: Comparison of MG with SU and DG Methods

Sperms were isolated using MG, SU and DG methods and tested for motility, morphology and DNA integrity with that of native sperms. Semen samples analyzed were either freshly collected from different donors or stored in liquid nitrogen. Motility of each spermatozoon was graded according to WHO guidelines as progressive (PM), non-progressive (NP) and immotile (IM). The majority of the population was comprised of sperms with low motility, although some samples had progressive motility (PR) up to 28% among the highest. The overall motility percent was observed to be average or lower, with approximately 52% of motility being high compared to samples with motility as less as 18%.

Figure 7:
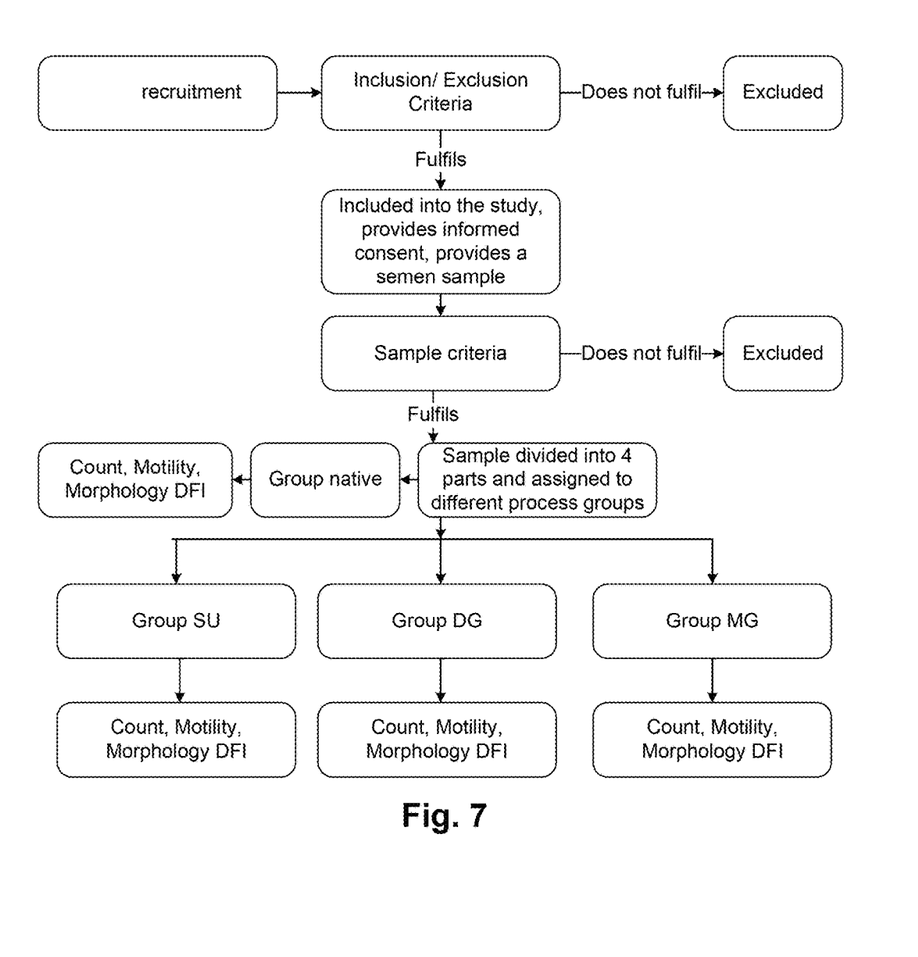
FIG. 7 is a flowchart indicating protocol for clinical studies, in accordance with an implementation of the present subject matter.

A flow chart of the clinical study is shown in FIG. 7. Fifty-five male partners of infertile couple met the inclusion/exclusion and additional sample criteria, and were recruited into the study. However, due to patient dropouts, experimental inadequacy, outliers, etc. the final number for analysis was reduced to 40. The mean±SD age of the subjects was 34.00±4.00 years. One outlier sample with unreasonably high DFI after processing by the three methods was excluded from analysis. The mean±SD and other descriptive statistics of routine semen analysis parameters and DFI of native (unprocessed) samples and sperm separated using method 100, DG and SU techniques are shown in Table 1.

TABLE 1

Semen analysis characteristics and DNA integrity of unprocessed (native) and processed sperm by different separation techniques.

| | Native | MG | Density Gradient | Swim up |
|---|---|---|---|---|
| Sperm count (millions/mL) | | | | |
| Mean ± SD | 73.15 ± 23.14*** | 26.00 ± 22.38 | 49.21 ± 31.76$ | 24.17 ± 24.45 |
| Range | 28-152 | 2-100 | 2-120 | 1-100 |
| Motility (%) | | | | |
| Mean ± SD | 43.05 ± 8.87 | 34.05 ± 23.18 | 59.45 ± 26.55** | 40.45 ± 25.70 |
| Range | 20-60 | 0-90 | 15-90 | 5-90 |
| Morphology (%) | | | | |
| Mean ± SD | 3.92 ± 1.94 | 3.91 ± 2.17§ | NA | NA |
| Range | 1-8 | 1-8 | | |
| DNA Fragmentation Index (%) | | | | |
| Mean ± SD | 36.99 ± 16.65*** | 20.94 ± 9.62 | 18.76 ± 12.11 | 22.29 ± 12.79 |
| Range | 9.53-77.97 | 6.21-61.14 | 4.21-58.87 | 4.95-53.18 |

Legend:
§Student's t-test value 0.99, One way anova using tukey's multiple comparison test-
**P < 0.01,
***P < 0.001,
$MG vs DG P < 0.001

It is observed from Table 1 that the mean, post-process sperm count is significantly different for the three separation techniques (P<0.001) in comparison with native unprocessed sample. However, the sperm count for MG technique remained in the same range as that of SU method. There was no significant difference between mean motility of native, MG, and SU methods. DG was significantly higher than MG and SU, although the range of motility remained same after processing by the three techniques. Morphology of sperms after MG method, in terms of percentage of normal forms, was found to be in the same range and was not significantly different (P=0.99) from that of native group. Mean DFI, an indicator of the DNA integrity of sperms, showed 43.4% reduction using MG technique as compare to native sample. The range of DFI values had become narrower compared to the native group after processing by the three methods.

Figure 8:
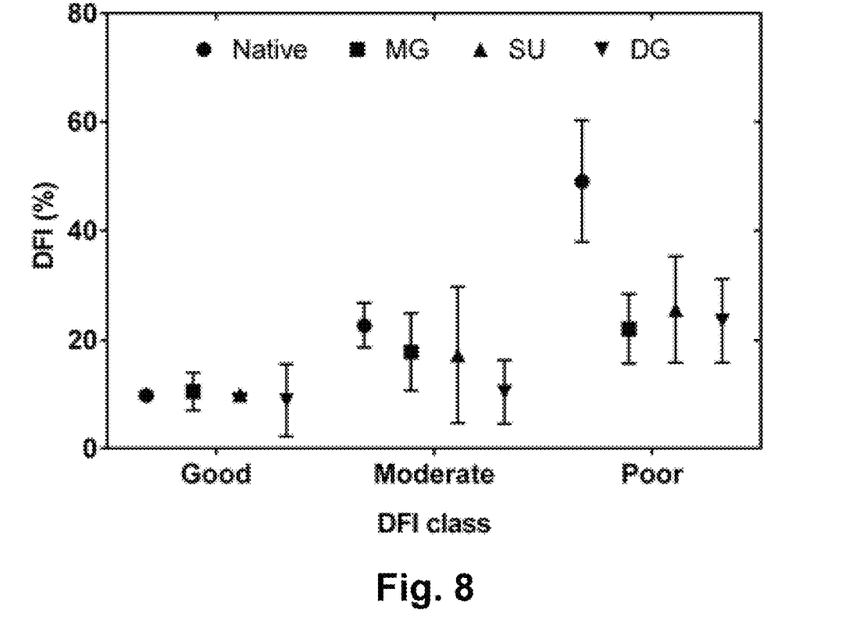
FIG. 8 is a graphical representation for DNA fragmentation Index (DFI) comparison with conventional techniques, in accordance with an implementation of the present subject matter.

FIG. 8 summarizes the variation in DFI of the sperms extracted using MG, SU and DG techniques. In order to study the improvement in DNA integrity of sperms separated by MG technique, subject population was classified into sub-groups based on DFI of native samples. As expected with good quality, low DFI samples in the first 'good DFI' sub-group, there was no significant improvement in DFI (P=0.83) after extraction by method 100. On the other hand, significant improvement in DFI is seen in 'moderate DFI' and 'poor DFI' subgroups, where it is much needed in order to enhance the success rates of ART for these patients. For the 'moderate DFI' subgroup, mean DFI decreased by 21.4% after MG (P=0.037). In this subgroup, 5 out of 14 (35.7%) samples showed improvement in DFI from 'moderate DFI' to 'Good DFI' class, and another 8 samples (57.1%) show improved DFI within the 'moderate DFI' class.

In case of 'poor DFI' subgroup, the improvement in DFI was highly significant (P<0.001), with 44.9% reduction after separation using MG technique. In 'poor DFI' class, except for two, all the samples showed improvement in the DFI classification. While 17 out of 22 samples (77.3%) improved to 'moderate DFI', two samples (9.1%) improved to 'good DFI' after separation by MG technique.

In this regard, the method 100 of the present subject matter is an easy, convenient and cost-effective method to select competent sperms with intact acrosomal status and better DNA integrity compared to native, unprocessed sperms and is comparable with SU technique (Table 1). Sperm-HA binding shows similarities to binding of the sperm to human zona pellucida, in that motile sperm with good nuclear morphology have superior binding to HA. In the present study, the motility and morphology of the sperms were retained after separation by method 100 (Motility: 43.05±8.87% for Native group vs. 34.05±23.18% for MG group, P=0.2679; Normal forms: 3.92±1.94% for Native vs. 3.91±2.17% for MG group, P=0.99). There was no significant difference in motility and sperm count by method 100.

Figure 9:
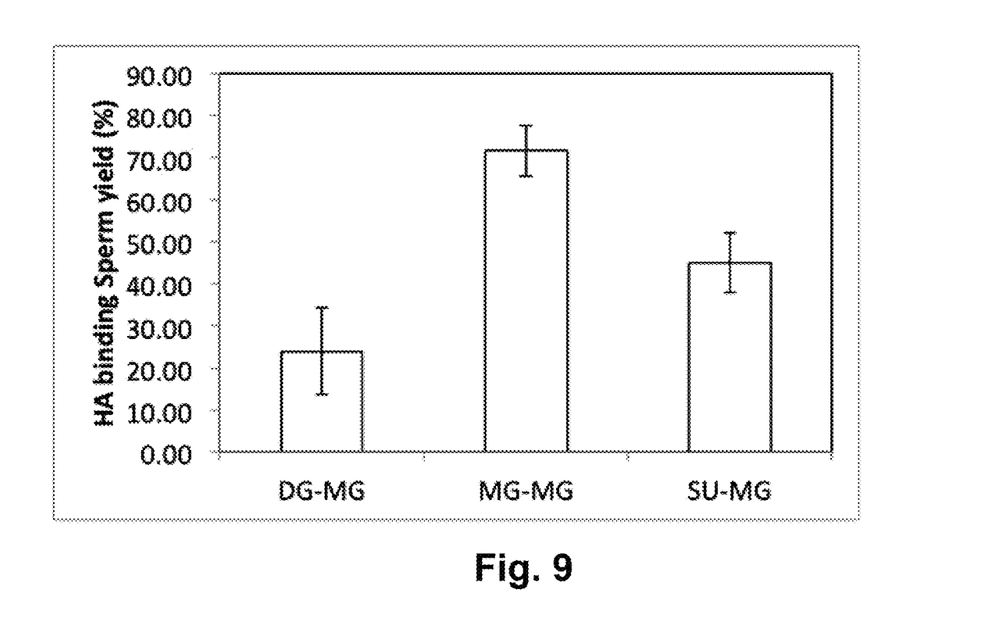
FIG. 9 is a graphical representation of HA-binding sperm yield variation with combination of method of present subject matter and conventional techniques, in accordance with an implementation of the present subject matter.

SU techniques and DG showed higher recovery than MG, however, binding/re-binding capacity of sperms isolated by MG was 199 and 59% more when compared to sperms isolated by DG and SU method respectively (FIG. 8 and FIG. 9). This indicates that all sperms isolated using DG and SU techniques are not viable. It has also been shown that sperms that are able to bind to HA are mature and have completed the spermiogenetic processes of sperm plasma membrane remodelling, cytoplasmic extrusion, and nuclear histone-protamine replacement.

Studies have shown that HA-bound human spermatozoa had intact acrosomes, mature nuclei, and better morphology with enhanced levels of developmental sperm maturity and higher sperm DNA integrity. In current study, the DFI of MG selected sperms, measured by flow cytometry using AO staining of DNA strands, has indicated considerable and statistically significant improvement over native, unprocessed sperm (P=0.001), and is similar to those purified by SU and DG methods (Table 1). The improvement in DFI is further evident during sub-group analysis shown in FIG. 8 and FIG. 9. The DFI range was 31.2-77.97% in native samples and 11.6-36% in MG samples for poor DFI class.

The method 100 of the present subject matter is a simple procedure that does not involve repeated centrifugation as with SU and DG methods, and yields sufficiently high count of mature sperms.

Although the subject matter has been described in considerable detail with reference to certain examples and implementations thereof, other implementations are possible. As such, the scope of the present subject matter should not be limited to the description of the preferred examples and implementations contained therein.

We claim:

1. A method for extracting viable sperms from a semen sample, the method comprising:
    incubating functionalized hyaluronic acid (HA) with functionalized paramagnetic beads to obtain a plurality of HA coated paramagnetic beads;
    incubating the plurality of HA coated paramagnetic beads with the semen sample to obtain a first population and a second population of sperm, wherein the first population comprises viable sperm bound to the plurality of HA coated paramagnetic beads and the second population comprises sperms not bound to the plurality of HA coated paramagnetic beads;
    magnetically drawing the first population away from the second population to separate the second population from the first population and to obtain a separated first population, wherein the separated first population comprises viable sperm bound to the plurality of HA coated paramagnetic beads;
    enzymatically degrading the HA with hyaluronidase enzyme to release the sperm from the paramagnetic beads in the separated first population; and
    magnetically drawing the paramagnetic beads away from the released sperms to obtain the viable sperms.

2. The method as claimed in claim 1, wherein the functionalized HA comprises biotin bound to HA.

3. The method as claimed in claim 1, wherein the functionalized paramagnetic beads comprise paramagnetic beads functionalized with one of streptavidin and avidin.

4. The method as claimed in claim 1, wherein the method comprises pre-washing the functionalized paramagnetic beads with phosphate buffered saline (PBS) before incubating with the functionalized HA.

5. The method as claimed in claim 1, wherein the method comprises washing the plurality of HA coated paramagnetic beads with phosphate buffer saline (PBS) comprising Bovine Serum Albumin (BSA) prior to incubation with semen sample.

6. The method as claimed in claim 1, wherein the first population and second population are separated by placing on a magnet stand.

7. The method as claimed in claim 1, wherein enzymatically degrading the HA comprises:
    incubating the separated first population with Sperm Wash Media (SWM); and
    adding the hyaluronidase enzyme during incubation of the plurality of HA coated paramagnetic beads with SWM to obtain released sperms.

* * * * *